United States Patent
Pedrazzi et al.

(10) Patent No.: US 7,147,616 B2
(45) Date of Patent: Dec. 12, 2006

(54) METHOD FOR EMPTYING A BLOOD CIRCUIT OF AN APPARATUS FOR THE EXTRACORPOREAL TREATMENT OF BLOOD

(75) Inventors: Renato Pedrazzi, Mirandola (IT); Paolo Rovatti, Finale Emilia (IT)

(73) Assignee: Gambro Hospal (Schweiz) AG, Basel (CH)

( * ) Notice: Subject to any disclaimer, the term of this patent is extended or adjusted under 35 U.S.C. 154(b) by 521 days.

(21) Appl. No.: 09/979,307

(22) PCT Filed: Jan. 12, 2001

(86) PCT No.: PCT/IB01/00027

§ 371 (c)(1),
(2), (4) Date: Mar. 18, 2002

(87) PCT Pub. No.: WO01/51106

PCT Pub. Date: Jul. 19, 2001

(65) Prior Publication Data

US 2003/0100857 A1   May 29, 2003

(30) Foreign Application Priority Data

Jan. 12, 2000   (IT) ................. TO2000A0025

(51) Int. Cl.
*A61M 37/00* (2006.01)
*C02F 1/44* (2006.01)
*A61L 2/16* (2006.01)
*A61L 101/00* (2006.01)

(52) U.S. Cl. .................. 604/6.16; 210/636; 210/644; 210/321.69; 422/28; 422/44; 604/6.09; 604/4.01

(58) Field of Classification Search ........ 210/645–646, 210/600, 634, 644, 739, 741, 416.1, 433.1, 210/321.6, 258, 636, 251, 252, 321.69; 604/5.04, 604/6.01, 6.1, 6.11, 6.15, 6.16, 4.01, 5.01, 604/21, 27, 30, 65–67; 422/44, 48, 1, 28
See application file for complete search history.

(56) References Cited

U.S. PATENT DOCUMENTS 4,695,385 A * 9/1987 Boag ......................... 210/636
4,955,508 A * 9/1990 Capanna et al. ............. 222/94

(Continued)

FOREIGN PATENT DOCUMENTS

DK  EP 0720856  7/1996
WO  WO 9015631  12/1990

*Primary Examiner*—Tatyana Zalukaeva
*Assistant Examiner*—Leslie Deak
(74) *Attorney, Agent, or Firm*—Finnegan, Henderson Farabow, Garrett & Dunner, L.L.P.

(57) ABSTRACT

A method for emptying a blood circuit of an apparatus for the extracorporeal treatment of blood after interrupting a treatment session. The apparatus has a blood treatment device with first and second compartments separated by a semi permeable membrane, an arterial pipe connected to an inlet of the first compartment, a venous pipe connected to an outlet of the first compartment and a second end, and a used liquid circuit having a drain pipe connected to an outlet of the second compartment. The method involves the closing of the blood circuit on itself. The blood circuit includes the arterial pipe, the first compartment of the blood treatment apparatus, and the venous pipe, in order to form a closed loop circuit after the arterial and venous pipes have been disconnected from the vascular system of the patient. The blood circuit contains a liquid, which is transferred from the closed loop circuit into the used liquid circuit. The liquid transferred into the used liquid circuit is then drained using the drain pipe.

14 Claims, 2 Drawing Sheets

Figure 1:
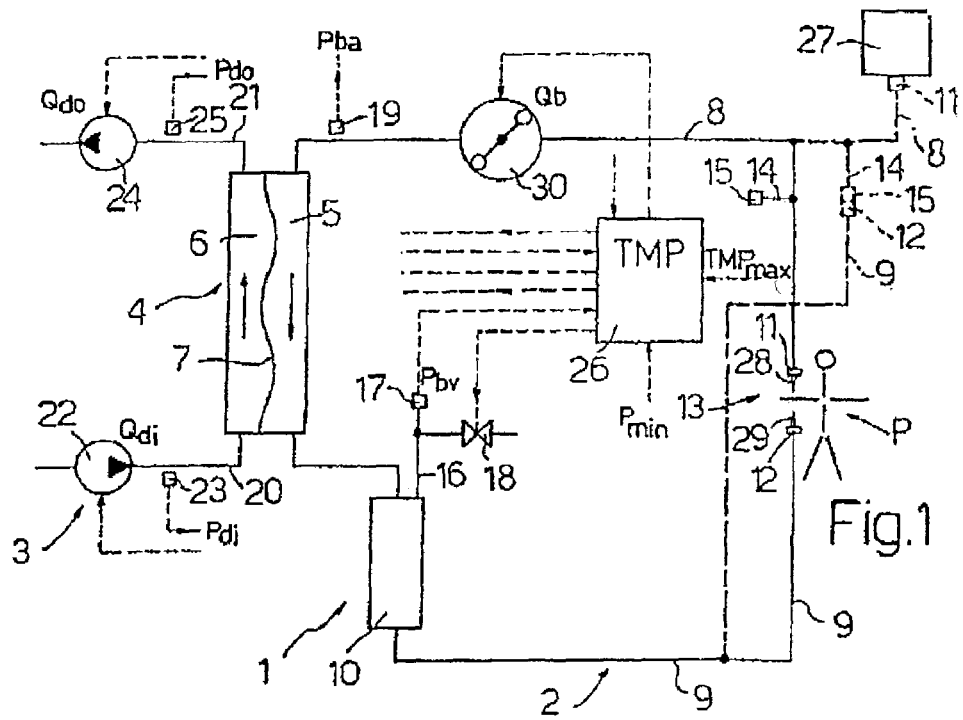

U.S. PATENT DOCUMENTS 5,043,074 A * 8/1991 Chevallet ..................... 210/646
5,484,397 A * 1/1996 Twardowski ............... 604/5.01
5,685,835 A * 11/1997 Brugger ..................... 604/6.06
5,772,624 A * 6/1998 Utterberg et al. .......... 604/4.01
5,776,091 A    7/1998 Brugger et al.
5,932,103 A    8/1999 Kenley et al.

* cited by examiner

METHOD FOR EMPTYING A BLOOD CIRCUIT OF AN APPARATUS FOR THE EXTRACORPOREAL TREATMENT OF BLOOD

The present invention relates to a method for emptying a blood circuit of an apparatus for the extracorporeal treatment of blood, at the end of a treatment session, when the blood contained in the circuit has almost been wholly returned to the patient who has undergone the treatment.

The invention is useful in any kind of treatment in which blood is continuously withdrawn from a patient, circulated and treated in a treatment device, and returned, once treated, to the patient. Hemodialysis, hemofiltration, apheresis and plasmapheresis are examples of such treatment, For the sake of clarity, the invention will be described hereunder in relation to a specific treatment, hemodialysis, to which however it is not limited as will readily appear to the persons skilled in the art.

A dialysis apparatus essentially comprises:

- a filter (dialyzer) having a first and a second compartments separated from one another by a semi permeable membrane;
- an extracorporeal blood circuit, having an arterial pipe connected to an inlet of the first compartment and a venous pipe connected to an outlet of the first compartment; a blood pump is arranged on the arterial pipe and a bubble trap is connected to the venous pipe;
- a dialysis liquid circuit, having a fresh dialysis liquid supply pipe connected to an inlet of the second compartment and a used liquid drain pipe connected to an outlet of the second compartment; a first pump is arranged on the supply pipe and a second pump is arranged in the drain pipe.

Each pipe of the extracorporeal blood circuit is fitted with a needle (respectively, arterial needle and venous needle), by means of which the extracorporeal circuit is connected to the patient: just before starting the treatment, the arterial needle and the venous needle are inserted in the fistula of the patient (portion of a vein surgically connected to an artery) for respectively collecting the blood to be treated and returning the treated blood to the patient's cardiovascular system.

In use, the blood of the patient and the dialysis liquid are respectively circulated in the first and the second compartments, generally in counterflow.

During a dialysis treatment, undesirable substances (by-products of the metabolism, such as urea, creatinine, etc.) contained in the blood migrate across the semi permeable membrane from the blood compartment to the dialysis liquid compartment by diffusion (dialysis phenomenon, strictly speaking) and also generally by convection, a fraction of plasma water being usually filtered during the treatment so that the patient loses a few kilograms (so-called "weight loss") corresponding to en excess of water accumulated in the body between two treatment sessions.

At the end of a dialysis treatment, the blood pump is stopped, the arterial needle is disconnected from the fistula of the patient, and the arterial pipe is connected to a bag containing a physiological saline solution. Then the blood pump is run so that the saline solution pushes the blood present in the blood circuit and the blood is returned to the patient. When the cloudy interface between blood and the saline solution reaches the venous needle, the blood pump is stopped and the arterial needle is disconnected from the fistula. Once disconnected from the dialysis liquid circuit, the dialyzer together with the arterial and venous pipes are discarded in a special container for contaminated waste since the residual blood contained in the blood circuit could be contaminated.

This way of ending a dialysis session with discarding the dialyzer connected to blood circuit full of liquid has various drawbacks, in particular as far as hygiene and the cost of treatment are concerned. The venous pipe, even closed by a clamp, risks dripping and soiling, with blood, the dialysis apparatus and the room in which the apparatus is installed and therefore contaminating the environment. Moreover since the disposal of contaminated, waste has an high cost per kilogram and the blood circuit is full of physiological saline solution and residual blood and is therefore heavy, the cost of disposal of a blood circuit is high and represents a significant portion of the overall cost of a dialysis treatment.

Another known method for ending a dialysis treatment consists in pumping air in the arterial pipe so as to push the blood contained in the dialyzer and blood circuit towards the venous needle and transfer the residual blood to the patient. This method is however fairly dangerous since it entails the risk, if the transfer of the residual blood is not stopped in time, to pump air into the patient's cardiovascular system. In fact, this method is no longer used owing to the risks for the patient.

The object of the present invention is to provide a method for emptying a blood circuit which is hygienic, safe for the patient, and less costly than the known methods.

According to the invention, a method for emptying a blood circuit of an apparatus for the extracorporeal treatment of blood, after interrupting a treatment session, comprises the steps of:

- closing on itself a blood circuit comprising the arterial pipe, the first compartment of the blood treatment apparatus and the venous pipe in order to form a closed loop circuit, after the arterial and venous pipes have been disconnected from the vascular system of the patient, the blood circuit containing a liquid,
- transferring the liquid contained in the closed loop circuit into the used liquid circuit, and
- draining the liquid transferred into the used liquid circuit using the drain pipe.

According to a characteristic of the invention, the step of transferring the liquid into the second compartment comprises the step of causing a pressure difference across the membrane of the blood treatment apparatus, the pressure being higher in the first compartment than in the second compartment, so as to cause the filtration of the liquid through the membrane from the first compartment to the second compartment.

According to another characteristic of the invention, the step of causing a pressure difference across the membrane of the blood treatment apparatus comprises maintaining the pressure difference slightly below a predetermined maximum pressure difference.

According to the invention, the method further comprises the step of opening the closed loop circuit to the atmosphere when the pressure in the venous pipe reaches a predetermined low value.

This method has the advantages of reducing the weight of the contaminated waste and of eliminating the problems caused by the liquid leaking from the blood circuit after use and contaminating the environment.

Figure 2:
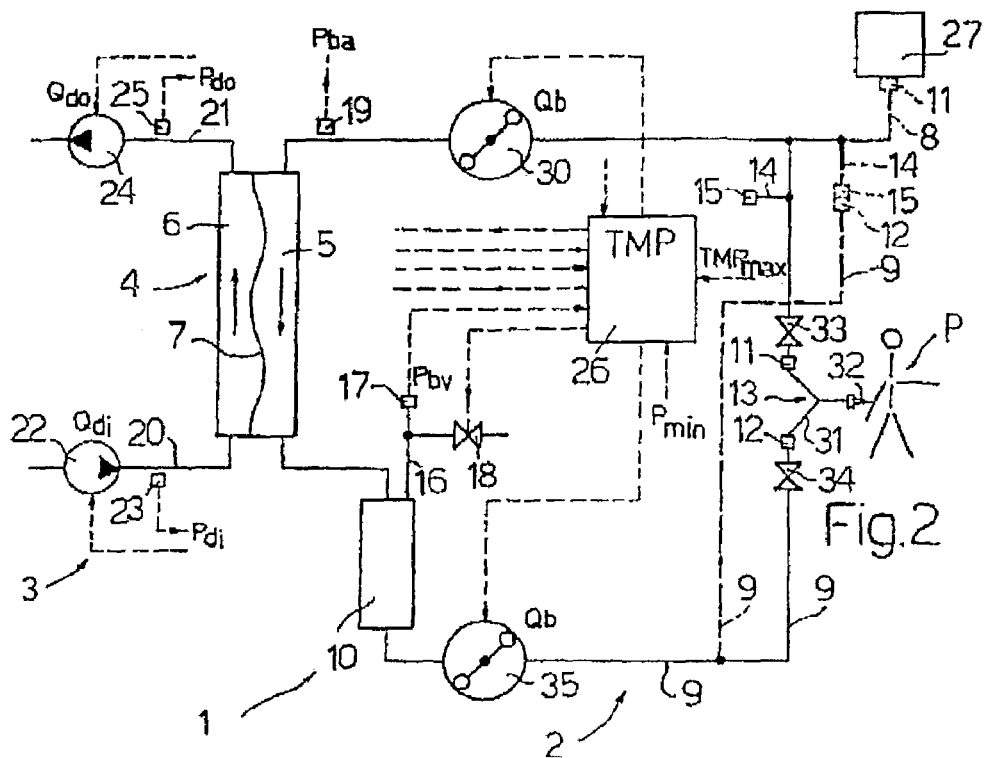
Figure 3:
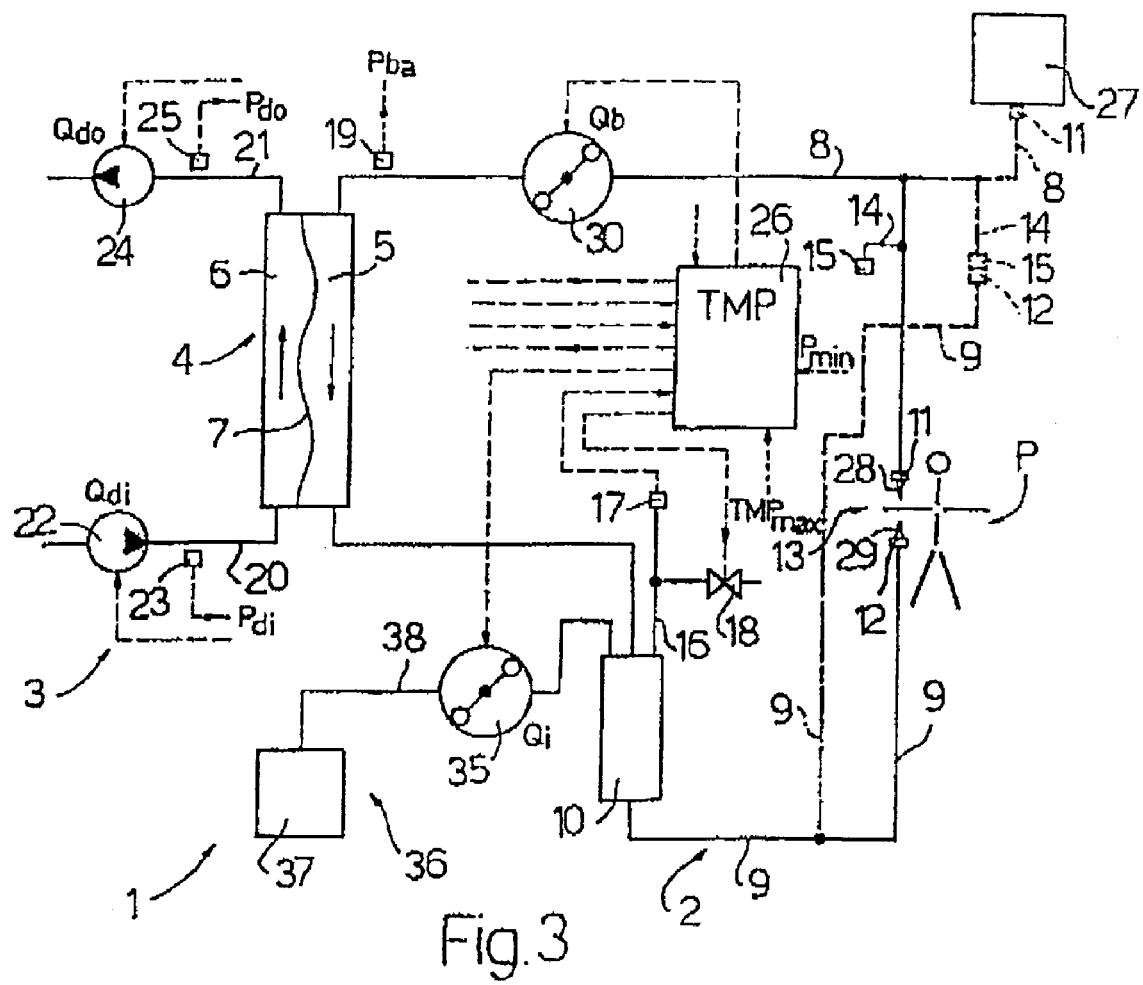

The invention will now be described in details. Reference will be made to the attached drawings in which:

FIG. 1 is a schematic view of a dialysis apparatus prepared for a dialysis treatment procedure and a procedure for emptying the blood circuit in accordance with the method forming the subject of the present invention;

FIG. 2 is a schematic view of the apparatus of FIG. 1 prepared for a second dialysis treatment procedure and a procedure for emptying the blood circuit in accordance with the method forming the subject of the present invention; and FIG. 3 is a schematic view of the apparatus of FIG. 1 prepared for a further dialysis treatment procedure and a procedure for emptying the blood circuit in accordance with the method forming the subject of the present invention.

FIG. 1 represents a dialysis apparatus 1, which comprises:
a dialyzer 4 having a first and a second compartments 5, 6 separated from one another by a semi permeable membrane 7,
a blood circuit 2 comprising:
 an arterial pipe 8 having a first end connected to an inlet of the first compartment 5 and a second end fitted with a connector 11 for an arterial needle 28,
 a venous pipe 9 having a first end connected to an outlet of the first compartment 5 and a second end fitted with a connector 12 for a venous needle 29,
a dialysis liquid circuit 3 comprising:
 a fresh dialysis liquid supply pipe 20 connected to an inlet of the second compartment 6,
 a used liquid drain pipe 21 connected to an outlet of the second compartment 6,
a control unit 26.

The arterial pipe 8 is fitted with a blood pump 30 for circulating blood at a flow rate Qb and with a pressure sensor 19 for measuring the blood pressure Pba immediately upstream of the dialyzer 4.

The venous pipe 9 is fitted with a bubble trap 10, connected to a pressure sensor 17 for measuring the blood pressure Pbv downstream of the dialyzer 4. The bubble trap 10 is also connected to a vent 16 the opening of which is controlled by a solenoid valve 18.

The dialysis liquid supply pipe 20 is fitted with a first pump 22 for circulating the dialysis liquid at a flow rate Qdi and with a pressure sensor 23 for measuring the pressure Pdi immediately upstream of the dialyzer 4.

The used liquid drain pipe 21 is fitted with a second pump 24 for circulating the used liquid at a flow rate Qdo and with a pressure sensor 25 for measuring the pressure Pdo immediately downstream of the dialyzer 4.

The control unit 26 is connected to a user interface (not represented) through which it receives instructions, such as various target flow rate values (blood flow rate Qb, dialysis liquid flow rate Qd and, where appropriate, infusion liquid flow rate Qi, treatment duration value T, and weight loss value WL). The control unit 26 furthermore receives information output by the measuring instruments of the system, namely the pressure sensors 17, 19, 23 25. On the basis of the instructions received and the operating modes and algorithms which have been programmed, it controls the active components of the system, such as the pumps 22, 24, 30 and the valve 18, According to the invention, a branch pipe 14 having a connector 15 at the end thereof is connected to the arterial pipe 8 upstream of the blood pump 30. A plug is mounted on the connector.

During a treatment session, the dialysis apparatus of FIG. 1, operates in a conventional way; the blood circuit 2 is connected to the cardiovascular system of the patient P, the arterial needle 28 and the venous needle 29 being inserted in the fistula of the patient P. The blood pump 30 is running, circulating blood in the blood circuit at a flow rate Qb. The two pumps 22 and 24 arranged on the dialysis liquid circuit 3 are running, the used liquid pump 24 running at a higher speed than the fresh dialysis pump 25, so as to cause a difference in pressure between the first and second compartment 5, 6 (transmembrane pressure TMP), the pressure in the second compartment 6 of the dialyzer 4 being lower than the pressure in the first compartment 5. As a result thereof, plasma water is filtered through the membrane 7 from the first into the second compartment and the programmed weight loss is achieved at the end of the treatment.

In order to end the treatment, the blood pump 30 is stopped for the time necessary for disconnecting the arterial pipe 8 from the patient P and for connecting it to a flexible bag 27 containing a sterile saline solution (the arterial pipe 8 connected to the bag 27 is shown in broken line). Then the blood pump is run again and the blood contained in the blood circuit is pushed by the sterile solution towards the venous needle 29 and is returned to the patient P. When the cloudy interface between the blood and the solution reaches the end of the venous pipe 9, the blood pump 20 is stopped.

According to the invention, in order to empty the blood circuit 9, which is then full of saline solution and residual blood, the venous pipe 9 is disconnected from the patient, the venous needle 29 is discarded and the end of the venous pipe 9 is connected to the branch pipe 14 by means of connectors 12 and 15, resulting in the blood circuit 2 being closed on itself (the venous pipe 9 connected to the branch pipe 14 is shown in broken line). The blood pump 30 is run again so as to circulate the saline solution in the closed loop circuit at a moderate flow rate. The two pumps 22 and 24 arranged on the dialysis circuit are then controlled by the control unit 26 so that the actual transmembrane pressure TMP in the dialyzer 4, as calculated from the signals Pdi, Pdo, Pba, Pbv, provided by the pressure sensors 23, 25, 19 17 to the control unit 26, is slightly below the maximum TMPmax for this type of dialyzer, which has been entered in the control unit 26 before the beginning of the treatment. In this operating mode, either the upstream pump 22 is stopped and only the downstream pump 24 is run, or both pumps are run at substantially different speeds, the speed of the downstream pump 24 being faster that the speed of the upstream pump 22. As a result, the liquid contained in the closed loop is transferred, by filtration through the membrane 7 from the first compartment 5 to the second compartment 6 of the dialyzer 4 and is then discarded through the drain pipe 21. The flexible bag 27 is rapidly emptied and deflates until it collapses, while the pressure in the blood circuit 2 gradually diminishes. When the signal Pbv from the venous pressure sensor 17 becomes equal to a minimum. threshold value Pmin (previously entered in the control unit 26), the control unit 26 causes the opening of the valve 18 so as to establish communication between the closed loop circuit and the outside and equalize the pressure inside the compartment 5 with the atmospheric pressure. The blood pump 30 is run so as to circulate the saline solution until the transfer of the solution through the membrane 7 is completed. Then all the pumps are stopped, the supply and drain pipes 20, 21 are disconnected from the dialyzer 4 and the dialyzer 5, the arterial and venous pipe 8, 9 and the flexible bag 27 can be discarded.

FIG. 2 represents a dialysis apparatus 1, which differs from the dialysis apparatus of FIG. 1 only in as much as it is designed to operate with only one needle 32 instead of two needles (so-called single needle system). The components of this dialysis apparatus which are specific to a single needle operation mode are:
a Y connecting pipe 31, the leg of which is connected to a needle 32, and the two arms of which are fitted with a connector for respective connection to the arterial pipe 8 and the venous pipe 9;

a clamp 33 arranged on the arterial pipe 8 close to the end thereof fitted with the connector 11;

a clamp 34 arranged on the venous pipe 9 close to the end thereof fitted with the connector 12;

a second blood pump 35 arranged on the venous line.

This single needle dialysis apparatus operates in a conventional manner, alternating blood withdrawal stages (arterial clamp 33 open, venous clamp 34 closed, arterial pump 30 running, venous pump 35 stopped) and blood returning stages (arterial clamp 33 closed, venous clamp 34 open, arterial pump 30 stopped, venous pump 35 running).

When it is decided to interrupt the treatment, both blood pumps 30, 35 are stopped for the time necessary for closing the arterial arm of the Y connecting pipe 31 with a clamp, for disconnecting the arterial line 8 from the Y connecting pipe 31 and for connecting the arterial pipe 8 to a bag 27 containing a sterile saline solution. Then the two blood pumps 30, 35 are run together at the same speed until the cloudy interface between the saline solution and the blood reaches the vicinity of the end of the venous pipe 9, upon which the two blood pumps 30, 35 are stopped. The venous pipe 9 is then disconnected from the Y connecting pipe 31 and is connected to the branch pipe 14 by means of connectors 12, 15. The closed loop circuit is then emptied from its content as described above with respect to FIG. 1, both blood pumps 30, 35 being run at the same speed during this final stage.

The dialysis apparatus represented in FIG. 3 is the same as the dialysis apparatus of FIG. 1, except that it further comprises means 36 for infusing a sterile solution into the blood circuit 2, namely an infusion pipe 38 connecting a container 37 for a sterile solution to the bubble trap 10 and an infusion pump 35 for circulating the sterile solution at a flow rate Qi.

The dialysis treatment performed by the dialysis apparatus 1 represented in FIG. 3 differs from the treatment described with reference to FIG. 1 in that a given quantity of infusion liquid is infused into the cardiovascular system of the patient P.

The process for interrupting the treatment and subsequently emptying the blood circuit is the same as described above with respect to FIG. 1.

According to a variant not shown, the solenoid valve 18 is replaced by a manually operated valve and, when the signal Pbv is less than the set value Pmin, the control unit 26 emits a visual and/or acoustic signal warning the operator that the valve must be opened.

According to a variant not shown, the blood circuit 2 comprises an expansion chamber located between the branch pipe 14 and the arterial pipe 8.

According to a further variant not shown, the branch pipe 14 is connected to the bag 27 and it is closed by a clasp. At the end of the dialysis treatment, the arterial pipe 8 is closed by a clamp at the vicinity of the arterial connector 11 and the arterial needle 28 is disconnected from the fistula of the patient P. Then, the clamp is removed from the branch pipe 14 and the saline solution contained in the bag 27 can be circulated in the blood circuit. When the cloudy mixture of blood and saline solution reaches the vicinity of the venous needle 29, the venous needle 29 is disconnected from the fistula of the patient P, is then removed from the venous pipe 9 and the connector 12 fitting the venous pipe 9 is connected to the connector 11 fitting the arterial pipe 8 so as to close the blood circuit 2.

The invention claimed is:

1. A method for emptying an extracorporeal blood circuit comprising the steps of:

providing a blood treatment device having a first compartment and a second compartment separated from one another by a semipermeable membrane, said first compartment being connected to a first pipe of an extracorporeal blood circuit and to a second pipe of said extracorporeal blood circuit, said first pipe and said second pipe being connected to a patient;

performing an extracorporeal blood treatment session in which blood is withdrawn from said patient, circulated and treated in said blood treatment device, and returned to said patient;

interrupting said blood treatment session;

after interrupting said blood treatment session, disconnecting said first pipe from said patient, connecting said blood circuit to a source of a solution, and returning blood from said blood circuit to said patient;

after said returning step, disconnecting said second pipe from said patient and forming a closed loop circuit, said closed loop circuit comprising said first compartment and a liquid, said liquid containing said solution and residual blood;

transferring said liquid through said semipermeable membrane from said first compartment to said second compartment; and discarding said first pipe and said second pipe.

2. A method according to claim 1, further comprising the step of draining said liquid transferred into said second compartment using a drain pipe connected to an outlet of said second compartment.

3. A method according to claim 1, wherein said transferring step comprises operating a pump connected to an outlet of said second compartment, and wherein during said transferring step a vent connected to said closed loop circuit is open.

4. A method according to claim 3, wherein during said transferring step, said closed loop circuit is open to the atmosphere through said vent.

5. A method according to claim 3, wherein during said transferring step, a communication between said closed loop circuit and the atmosphere is established through said vent.

6. A method according to claim 3, wherein said vent is connected to a bubble trap of said extracorporeal blood circuit.

7. A method according to claim 3, wherein said vent is connected to the atmosphere.

8. A method according to claim 3, wherein the opening of said vent is controlled by a valve.

9. A method according to claim 3, wherein said transferring step further comprises the step of opening said vent when the pressure in said closed loop circuit reaches a predetermined low value.

10. A method according to claim 3, further comprising the step of opening said vent.

11. A method according to claim 1, wherein during said transferring step, a pressure inside said first compartment is equalized with the atmospheric pressure.

12. A method according to claim 1, wherein said step of forming a closed loop circuit comprises connecting said second pipe to a branch pipe of said first pipe.

13. A method according to claim 1, wherein said step of forming a closed loop circuit comprises connecting a patient vascular system connection end of said first pipe to a patient vascular system connection end of said second pipe.

14. A method according to claim 1, wherein said transferring step further comprises causing a pressure difference across said semipermeable membrane, wherein a pressure in said first compartment is higher than a pressure in said second compartment, and wherein said pressure difference is maintained below a predetermined maximum pressure difference.

* * * * *